United States Patent [19]

Sportsman et al.

[11] Patent Number: 5,830,918
[45] Date of Patent: Nov. 3, 1998

[54] NONPEPTIDE INSULIN RECEPTOR AGONISTS

[75] Inventors: Richard Sportsman, San Francisco; Hugo O. Villar, Newark; Lawrence M. Kauvar, San Francisco, all of Calif.

[73] Assignee: Terrapin Technologies, Inc., South San Francisco, Calif.

[21] Appl. No.: 784,857

[22] Filed: Jan. 15, 1997

[51] Int. Cl.⁶ .................................................. A61K 31/135
[52] U.S. Cl. ............................................................ 514/648
[58] Field of Search ............................................. 514/648

[56] References Cited

U.S. PATENT DOCUMENTS

| 5,217,869 | 6/1993 | Kauvar | 435/7.9 |
| 5,300,425 | 4/1994 | Kauvar | 435/7.9 |
| 5,587,293 | 12/1996 | Kauver et al. | 435/7.21 |

OTHER PUBLICATIONS

Brinkworth, R. I., et al., "Non–Peptidic Anti–Aids Agents: Inhibition of HIV–1 Proteinase by Disulfonates" *Biochem Biophys Res Comm* (1992) 188:624:630.

Kirchberger, J. et al., "Studies of the Interaction of NADH Oxidase from Thermus Thermophilus HB8 with Triazine Dyes" *J Chromatog A* (1994) 668:153–164.

Kletzien, R. F., et al., "Enhancement of Adipocyte Differentiation by an Insulin–Sensitizing Agent" *J. Mol Pharmacol* (1992) 41:393–398.

Kobayashi, M. Pioglitazone Increases Insulin Sensitivity by Activating Insulin Receptor Kinase *Diabetes* (1992) 41:476–483.

*Primary Examiner*—Kevin E. Weddington
*Attorney, Agent, or Firm*—Morrison & Foerster LLP

[57] ABSTRACT

Modulation of the activity of the insulin receptor, enhancement of glucose uptake by cells, and other effects significant in the control and management of diabetes are accomplished using compounds of the formula

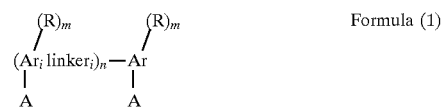

Formula (1)

wherein each Ar is independently an aromatic moiety;
each A is independently a proton-accepting substituent;
each R is independently a noninterfering substituent;
m is 0 or 1;
n is 4–6; and
each linker is independently an isostere of —$CH_2$—, —CH=CH— or —NCHO—. Compounds in the genus of Formula (1) can also be used for structure activity studies to identify features responsible for the relevant activities.

10 Claims, 10 Drawing Sheets

TER 12

TER 3938

TER 3935

TER 16998

NONPEPTIDE INSULIN RECEPTOR AGONISTS

TECHNICAL FIELD

The invention relates to the substitution of nonpeptide compounds for peptide ligands that activate hormone receptors. More specifically, it concerns simple nonpeptide compounds that behave as agonists for the insulin receptor and enhance the effect of insulin on this receptor.

BACKGROUND ART

Among the many functions performed by peptides and proteins in metabolism is the ability to stimulate receptors at cell surfaces to effect intracellular consequences important in maintenance and development of the organism. Peptide and protein hormones interact with receptors specific for them so that the activity of the hormone is felt on designated cells exhibiting these receptors. The insulin receptor is present on virtually all cells and at high concentrations on the cells of the liver, skeletal muscles, and adipose tissue. Stimulation of the insulin receptor with insulin is an essential element in carbohydrate metabolism and storage.

Diabetics either lack sufficient endogenous secretion of the insulin hormone (Type I) or have an insulin receptor-mediated signaling pathway that is to some degree resistant to endogenous or exogenous insulin, either through primary or post-translational structural changes, reduced numbers or poor coupling among signaling components (Type II). All Type I diabetics, and many Type II subjects as well, must utilize injection to obtain enhanced activity of the extant insulin receptors, since endogenous insulin can at present be replaced only with an alternative supply of insulin itself, previously isolated from native sources, and now recombinantly produced. While the recombinant production of insulin permits a less immunogenic form to be provided and assures a reliable supply of needed quantities, the necessity to administer the hormone by injection remains, due to the instability of peptides and proteins in the digestive tract. It has long been the goal to substitute for peptide ligands, including insulin, small molecules which are not digested and can be absorbed directly into the bloodstream. However, to date, nonpeptide substances which can exert the effect of insulin on its receptor have eluded discovery.

There have been many instances in which nonpeptide materials have been used to inhibit enzymes whose native substrates are peptides. For example, Brinkworth, R. I. et al. *Biochem Biophys Res Comm* (1992) 188:624–630 describe the inhibition of HIV-1 proteinase by various aryl disulfonates. The ability of triazine dyes to bind NADH oxidase from Thermus thermophilus was studied by Kirchberger, J. et al *J Chromatog A* (1994) 668:153–164.

It has also been shown that certain nonpeptide components enhance the agonist properties of a peptide hormone, The ability of certain thiazolidinediones such as pioglitazone to enhance adipocyte differentiation by stimulating the effect of insulin has been described by, for example, Kletzien, R. F. et al. *J Mol Pharmacol* (1992) 41:393–398. These represent a class of potential antidiabetic compounds that act at an unknown site downstream from the insulin receptor itself and enhance the response of target tissues to insulin. Kobayashi, M. *Diabetes* (1992) 41:476–483. It is now known that most of the thiazolidinediones bind to PPARγ thus triggering certain nuclear events that may result in enhanced sensitivity of the target cells to insulin. However, the complete mechanism is still unresolved.

In any event, it has not as yet been possible to utilize simple molecules to provide the effect of a peptide hormone by stimulating receptor activity independently of the peptide hormone binding site.

It has now been found that several aryl di- or polysulfonate compounds which share certain common structural features are able to effect stimulation of the insulin receptor to activate the autophosphorylation activity required for signal transduction. The availability of these compounds permits construction of assays and comparative procedures for evaluating additional candidate compounds as well as the design and synthesis of therapeutics for primary treatment of insulin resistance and diabetics with the appropriate structural features.

DISCLOSURE OF THE INVENTION

The invention takes advantage of the behavior of, and information provided by, certain compounds, whose synthesis is straightforward, in order to conduct assays for the ability of candidate small molecules to activate the insulin receptor and to design these candidates. The method of identifying a primary member of this group, TER12 and of obtaining the remaining members is described below. These small molecules represent the first instance of direct agonist activity on the insulin receptor by a nonpeptide. Compounds identified in this way are useful in the control and management of diabetes in suitable subjects.

Thus, the invention is directed to methods to modulate the kinase activity of the insulin receptor or the kinase portion thereof; to potentiate insulin activation of the insulin receptor; to potentiate glucose uptake stimulation by insulin; to lower blood glucose; and to stimulate glucose uptake per se in cells by use of compounds having the formula

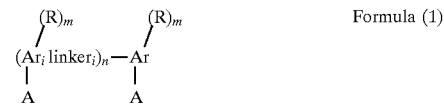

Formula (1)

wherein each Ar is independently an aromatic moiety;

each A is independently a proton-accepting substituent;

each R is independently a noninterfering substituent;

m is 0 or 1;

n is 4–6; and each linker is independently an isostere of —$CH_2$—, —CH=CH— or —NHCO—.

These compounds are thus useful in regulating the glucose metabolism of mammalian subjects which are afflicted with diabetes.

In another aspect, the invention is directed to a method to screen candidate compounds for ability to activate the insulin receptor. The method comprises first obtaining a fingerprint of each candidate with respect to a reference panel and obtaining a fingerprint of an activator which is Component A with respect to the same reference panel. Then the fingerprint of each candidate is compared with that of Component A. Successful candidates are compounds whose fingerprints resemble that of Component A.

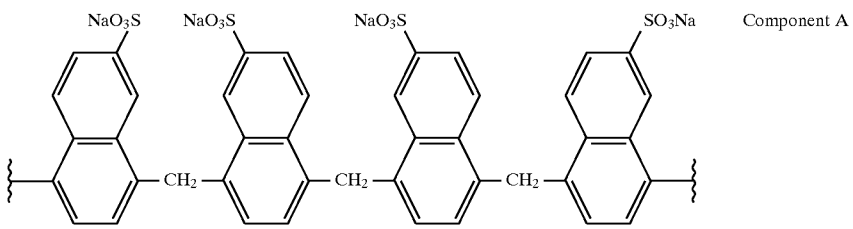

In another aspect, the invention relates to a method to design and synthesize a molecule that exhibits agonist activity or insulin agonist stimulating activity with respect to the insulin receptor. This method comprises assessing an activator identified as Component A structural features which correlate with said activities. Compounds containing these structural features are designed and synthesized.

In still another aspect, the invention provides an alternative method to identify a candidate compound which will activate the insulin receptor. This method comprises contacting a sample containing at least the kinase portion of the insulin receptor with an activator which is Component A in the presence and absence of said candidate.

The binding of said activator is then measured in the presence and absence of said candidate. For a successful candidate, the binding of activator is diminished in its presence as compared to its absence.

BRIEF DESCRIPTION OF THE DRAWINGS

FIG. 2A shows the structure of TER12, Cibacron Brilliant Red 3BA; FIG. 2B shows the structure of TER3938, Direct Yellow 27; FIG. 2C shows the structure of TER3935; FIG. 2D shows the structure of TER16998.

MODES OF CARRYING OUT THE INVENTION

Figure 1:
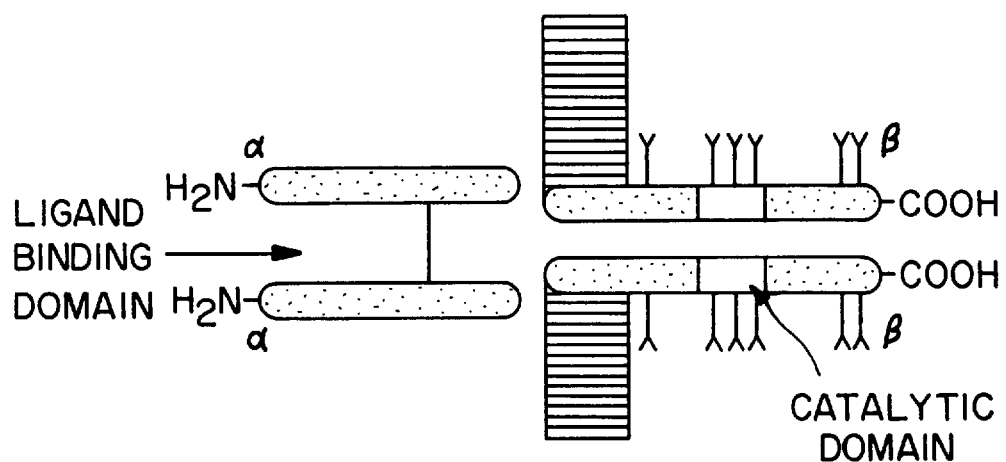
FIG. 1 shows a schematic diagram of the insulin receptor and its activation by insulin.

The structure of the insulin receptor and some aspects of its mode of action as currently understood, are illustrated in FIG. 1. The receptor consists of four separate subunits consisting of two identical α and two identical β chains. The two β chains contain a cross-membrane domain; the α portions are in the extracellular domain and accommodate the binding of insulin. The illustration in FIG. 1 shows insulin bound to the receptor. The β subunits contain a tyrosine kinase activity, shown as the white inserts into the subunits and the kinase of one β subunit effects the phosphorylation of the complementary β subunit as shown; the receptor illustrated in FIG. 1 is in its activated form when the tyrosine residues (Y) are phosphorylated. The β subunits also contain ATP binding sites. The insulin-stimulated phosphorylation of the receptor itself is required for subsequent activity and thus demonstration of the ability of a compound to effect phosphorylation of the β subunits provides a means to assay activation of the receptor.

The invention, in general, is directed to methods to regulate and manage subjects with diabetes by virtue of administering compounds which affect the activity of the insulin receptor. Without intending to be bound by any theory, it is believed that the compounds useful in the methods of the invention act directly on the kinase function of the receptor and do not necessarily compete with insulin for binding at the insulin-binding site, nor do they effect activation of the receptor by a mechanism similar to that exhibited by insulin. The compounds of the invention are able directly to activate the kinase of the receptor to autophosphorylate, to potentiate the effect of insulin on the receptor, to activate the kinase function of the receptor in phosphorylating exogenous substrates, to effect the increased uptake of glucose by adipocytes and insulin receptor-bearing cells in general, and to lower blood glucose levels in diabetic subjects.

The compounds of the invention are generally of the formula

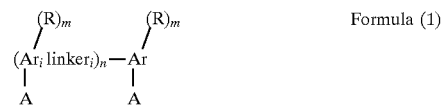

wherein each Ar is independently an aromatic moiety;
each A is independently a proton-accepting substituent;
each R is independently a noninterfering substituent;
m is 0 or 1;
n is 4–6; and
each linker is independently an isostere of —CH$_2$—, —CH=CH—, or —NHCO—.

In the compounds of Formula (1), the proton-accepting substituents represented by "A" may be anionic or may be sufficiently nucleophilic to accept a proton at physiological pH. Particularly preferred embodiments of A include —SO$_3$X, OP(OX)$_3$ and —COOX where X is a hydrogen atom or a cation depending on pH. Suitable cations include inorganic cations such as sodium, potassium, calcium and the like or may be organic cations such as those provided by organic bases, for example, caffeine. Also included in embodiments of A are amino substituents including primary, secondary, and tertiary amines. Typical bioisosteres of anionic ligands such as tetrazole rings, even when they are not charged.

The aromatic moieties represented by Ar are monocyclic or bicyclic aromatic systems such as benzene or naphthalene or contain one or more heteroatoms selected from the group consisting of O, S and N. Thus, included among the aromatic systems are benzothiazoles, quinolines, pyridine, and the like. Particularly preferred are naphthylene residues.

The noninterfering substituents on the naphthyl moieties in Formula (1) may or may not be present—i.e., each m is independently 0 or 1. The position of R is arbitrary in each case; preferred embodiments of R include substituted or unsubstituted hydrocarbyl moieties, whether straight-chain, branched or cyclic and whether aromatic or nonaromatic. Among these are included but not limited to alkyl substituents of 1–6C, alkenyl substituents of 1–6C, and alkyl or alkenyl substituents wherein the carbon chain is interrupted by one or more heteroatoms such as O, N or S. Substituents may also be of the formula —OR', —NR'$_2$ and —SR', wherein R' is H or is R as defined above. Particularly preferred embodiments include alkyl (1–6C).

In the compounds of Formula (1), each linker is independently an isostere of —CH=CH— such as —N=N—, —CH=N— or —CH$_2$CH$_2$— —NHCH$_2$, or —CH$_2$— such as NH or O, or of —NHCO— such as —OCO— or —COO—. General methods for forming all of these linkages between aromatic systems are well known in the art.

Particularly preferred compound of Formula (1) are those wherein each R is alkyl (1–6C). Also preferred are compounds of Formula (1) wherein each m is 0.

Also preferred are embodiments wherein the compound of Formula (1) is

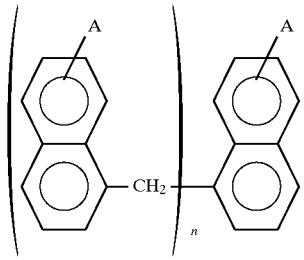

wherein n is 4–6 and A is as defined in claim 1.

Particularly preferred is the compound shown as Component A.

In addition to protocols to control diabetes in relevant subjects, the invention is directed to methods to identify additional compounds which are useful in these protocols. In general, such methods include identifying an active compound by a screening process that utilizes a set of maximally diverse candidate compounds. This method comprises, in a preferred embodiment, contacting each member of a set of maximally diverse candidate compounds with said receptor or kinase portion thereof; detecting the presence or absence of tyrosine phosphate on the receptor or kinase portion contacted with each set member; and identifying as a successful candidate at least one member of the set wherein an increased amount of tyrosine phosphate is detected in the receptor or kinase with which it was contacted, relative to untreated receptor.

In addition, once a compound with at least moderate ability to activate the kinase activity of insulin receptor has been identified, additional compounds can be identified by comparing the properties of the candidates with those of compounds having known activity. One particularly useful property to compare is the affinity fingerprint of the compound against a reference panel of proteins which provide a first approximation of the binding modes of all proteins. This is described in U.S. Pat. No. 5,587,293, incorporated herein by reference. Further, analysis of compounds shown to activate the insulin receptor kinase using standard structure activity analysis will result in additional compounds which behave as activators. Compounds identified as activators of the receptor in any of the foregoing three ways can further be used in competitive analyses with respect to additional candidate compounds, particularly if radiolabeled. Receptor mutagenesis and photoaffinity analogs may also be used to identify the receptor site binding the compounds, for use in rational drug design.

The three primary methods of identification of compounds with the desired IR kinase modulating activity are illustrated below.

The activator compounds are able to stimulate the phosphorylation catalyzed by IR kinase alone, i.e., to behave as agonists with respect to the receptor and/or are able to enhance the ability of insulin to effect phosphorylation of the receptor. Either of these effects can be considered an activation of the insulin receptor. Thus, by "activating" the insulin receptor is meant either the ability to behave as an agonist or the ability to enhance the stimulation by insulin or other agonists of the receptor activity. Both of these effects can be evidenced by autophosphorylation of the receptor.

The compounds of the invention evidently do not interact with the receptor at the native insulin binding site, but rather at a site located on the kinase portion of the receptor. Thus, these compounds define a newly discovered activation site for this receptor. This permits not only the identification of compounds with similar activities through competitive binding assays with the identified compound (which directly identifies compounds which interact with the same site), but also permits these assays to be conducted with forms of the receptor containing only the kinase portions.

Identification of Desired Activator Compounds—Maximally Diverse Libraries

A traditional approach to the identification of a substance which binds to a desired target is through simple trial and error. Done in a random fashion with each compound available in a chemical library, this approach is labor- and time-intensive for a complex assay such as autophosphorylation of IRk. As previously described by two of the present inventors, the number of trials can be minimized by testing only representative substances across the totality of chemical space. Thus, only members of a maximally diverse set of candidate compounds is tested in the trial and error procedure. One way to construct a maximally diverse set of candidates is described in U.S. Pat. 5,340,474, incorporated herein by reference. In this approach, the members of the set are synthesized from subunits wherein the subunits are chosen to result in a systematic variation of parameters, such as hydrophobicity, hydrophobic moment and the like, which determine the position of the resulting compound in chemical space. Alternatively, the maximally diverse set of test compounds can be obtained by manipulating affinity fingerprints. The fingerprints of multiple members of a compound library can be searched and clustered to obtain groups with similar fingerprints. Each group represents a different general location in chemical space. Iterations of this process may be continued until a manageable number of compounds representing the totality of chemical space are identified. Thus, from a cluster of, for example, fingerprints for 100 compounds with similar properties, only one of these 100 compounds need be included in the group of compounds to be tested for binding to the target. This is described in U.S. Pat. No. 5,587,293, cited above.

Figure 2A:
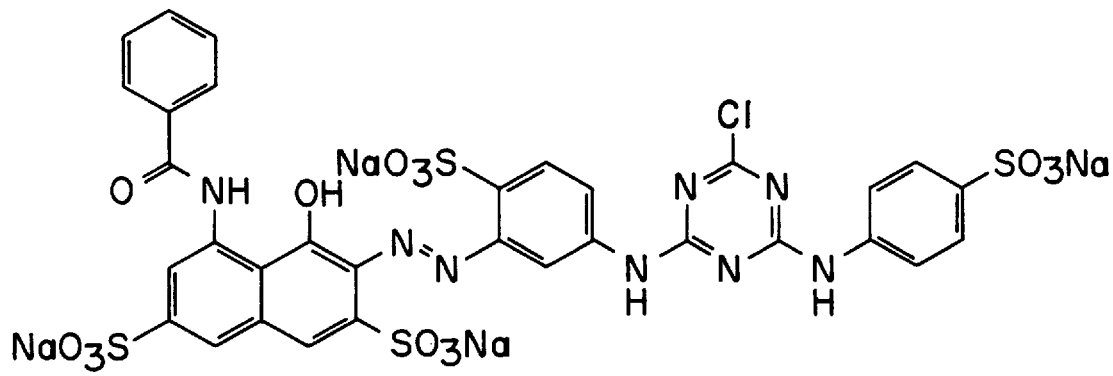
FIGS. 2A–2D show the structures of several compounds relevant to the invention which activate the insulin receptor.

In the present application, a library containing the fingerprints of 10,000 compounds obtained against a panel of 18 reference proteins was sorted as described, i.e., clusters of fingerprints with similar characteristics were grouped to select 50 representative compounds as a "training set." Each of these 50 representative compounds was tested with respect to the insulin receptor. A sample believed to consist only of TER12 shown in FIG. 2A, whose fingerprint did not group and was not a member of a cluster was the only tested compound that was successful in activating this receptor using the assay set forth in Example 1. Although it was later found that the component of the tested sample that had the structure of TER12 was not as active in this assay as a Component A, present at lower concentration, the structural similarities of TER12 and the actual active component are evident.

Fingerprint Comparison

Chemical catalogs were searched for compounds with structural features similar to those of TER12 or which when tested had fingerprints showing essential matching features. Of 42 compounds identified as having similar substructures, four showed activity with respect to the receptor; among these was a sample containing TER3938 shown in FIG. 2B, although most of the activity was later shown to be due to Component A present at lower concentration.

The fingerprints of these compounds identified with respect to a standard reference panel (further described hereinbelow) can be used as standards for comparison to fingerprints of candidate compounds likely to have the same activities.

U.S. Pat. No. 5,217,869 and 5,300,425, the contents of which are incorporated herein by reference, describe techniques for identifying compounds with similar properties by comparing their fingerprints. Briefly, a fingerprint for a single compound (which characterizes it) is obtained by testing the binding or reactivity of the compound with respect to a reference panel of substances which may, for instance, be antibodies or other substances which exhibit varied degrees of reactivity with respect to most compounds. The reference panels are chosen so that they represent virtually the totality of chemical space—i.e., a set of substances so varied in its spatial and charge contours that the ability to react with any other substance is contained at least somewhere within the panel. Each compound reacted with the panel, then, yields a characteristic pattern of reactivities which could be considered a fingerprint. Compounds which exhibit similar fingerprints exhibit similar patterns of reactivity and properties. Thus, if a target receptor is known to bind to a specific ligand, one can identify a compound which also binds to the receptor by choosing a compound whose fingerprint is similar to that of the known ligand. Here, the fingerprints of candidates from, for example, libraries of compounds are compared to the corresponding fingerprints of TER12, TER3938 or preferably Component A.

Structure Activity Relationships

Assessment of the structural features of an individual active compound, especially those that are shared by several active compounds, in contrast, for example, to the compounds which do not activate the insulin receptor, permits the design of suitable candidates for synthesis and testing. Methods for such analysis and identification of such structural features are known in the art. See, for example, Nesnow, S. et al. *J Toxicol Environ Health* (1988) 24:499–513, which describes the assignment of structural features among a group of 36 arylazo dyes as related to their ability to be reduced by rat liver microsomal azoreductase.

Competitive Binding

Once activators of the insulin receptor such as Component A (or any receptor) have been identified either by screening a maximally diverse library or by using the results of such screening to compare fingerprints and selecting fingerprints similar to those of the successful compounds, or by structure activity analysis of one or more activator compounds in comparison to those which are inactive, these successful activator compounds can be used to screen for additional substances which behave using similar mechanisms by competitive binding assays wherein the activator compounds, for example labeled with radioisotopes, fluorescent labels, enzyme labels, and the like, are contacted with the insulin receptor or the insulin receptor kinase in the presence and absence of candidate insulin receptor activator compounds. The amount of label bound to the receptor or to its kinase portion is measured in the presence and absence of the candidate; an increased level of label binding in the absence, as opposed to the presence of the candidate indicates that the candidate successfully competes for the newly defined binding site and is a successful candidate as an activator of the receptor.

The following examples are intended to illustrate but not to limit the invention.

EXAMPLE 1

Apparent Effect of TER12 on Insulin Receptor Kinase Autophosphorylation

A. This assay is a modified form of that described in Hagino, H. et al. *Diabetes* (1994) 43:274–280. Briefly, human insulin receptors (hIR) were partially purified from placental extracts or from cell line IM-9. The partially purified hIRs were captured into microplate wells by incubating them for 90 minutes with wells coated with a monoclonal antibody to hIR. The wells were then treated with various dose levels of insulin and/or test compounds for 15 minutes at room temperature; ATP (10 $\mu$M) was then added to permit kinase activity to proceed. After 60 minutes, the wells were washed, and then treated for 60 minutes with biotinylated antibody directed against phosphotyrosine (PY-20) and unbound materials again washed away. The wells were then incubated with a conventional streptavidin peroxidase system for 30 minutes to assess the level of phosphorylated tyrosine.

When tested in this assay, insulin gave a dose response curve showing an $EC_{50}$ of about 0.3 nM and a maximal activity at about 100 nM. The $EC_{50}$ is similar to that obtained for binding of labeled insulin to various cells and tissues.

Two sets of compounds of 50 members each, selected to be maximally diverse, as defined in U.S. Pat. No. 5,300,425 and incorporated herein by reference, were screened in the foregoing assay. Of these 100 compounds, only a sample composed mainly of TER12 (see FIG. 2A) showed apparent agonist activity. In the absence of insulin, 20 $\mu$M of this sample stimulated autophosphorylation over five-fold (0.3 nM insulin stimulates phosphorylation approximately to this extent). Thus, the activity of insulin at approximately 0.3 nM is roughly equivalent to that shown by this sample at approximately 20 $\mu$M and a component of this sample shows the ability directly to stimulate autophosphorylation.

In addition, the sample enhanced the ability of insulin to stimulate autophosphorylation. The addition of 60 $\mu$M sample to hIR contacted with 0.3 nM insulin resulted in an increase in phosphorylation of approximately three-fold and to the maximal level shown by insulin stimulation at higher concentrations. The $EC_{50}$ for this effect (enhancing insulin stimulation) was shown in additional experiments to be approximately 20 $\mu$M of sample calculated as TER12. These results were also confirmed by Western blot assay.

B. In an additional demonstration of the activity of a component in the sample containing TER12, the artificial substrate, poly($Glu_4Tyr$) was used as the substrate for phosphorylation. Incorporation of labeled phosphate from $\gamma$-labeled ATP was measured following activation of receptor prepared as in Paragraph A. About 20 μM of sample calculated as TER12 provided 75% of maximal insulin-stimulated activity; it also enhanced the ability of 0.5 nM and 5.0 nM insulin to effect phosphorylation; 0.5 nM insulin alone showed 60% maximal phosphorylation; addition of 20 μM of the TER12 sample increased this to 120%; in the presence of 5 nM insulin phosphorylation rose from 95% of maximum to 140%.

C. When tested with respect to insulin receptor agonist activity on whole cells, i.e., on the human lymphocytic cell line IM-9, the sample containing TER12 retained its ability to stimulate the receptor. In this assay, $2 \times 10^7$ cells were treated with and without this sample and with and without insulin for 5 minutes, followed by three washes in isotonic medium to remove the sample containing TER12. The cells were then lysed in 0.5% Tween 20 and lysates analyzed in an ELISA assay as described in Paragraph A, without the steps of incubation with ATP. After 5 minutes exposure to sample containing 20 μM TER12, basal insulin receptor kinase activity was increased two-fold and insulin stimulated insulin receptor kinase activity was increased five-fold.

D. The assay described in paragraph B was conducted by substituting, for the human insulin receptor, a recombinantly produced β chain lacking the insulin-binding domain (supplied by Stratagene, Inc.). The ability of this kinase to phosphorylate a substrate peptide (Raytide from Oncogene Sciences) is stimulated by TER12 at 25 μM. (In addition, a known inhibitor believed to act at the ATP site on the kinase also inhibits this modified form of the receptor.)

E. Insulin is able to induce the differentiation of 3T3-L1 fibroblast cells to an adipocyte-like morphology as measured by Oil Red O uptake. The sample containing TER12 alone does not appear to effect differentiation; however, at a concentration of 20 μM it enhances the differentiating effect of insulin. This activity is similar to that exhibited by pioglitazone described above. Insulin also enhances glucose transport in this cell line. Again, the sample alone failed to stimulate glucose transport significantly, but enhanced the ability of insulin to do so.

EXAMPLE 2

Additional Compounds with TER12-Like Activity

Using substructure searching based on the TER12 molecule, 42 candidate compounds were obtained and assayed according to the procedure of Example 1.

Figure 2B:
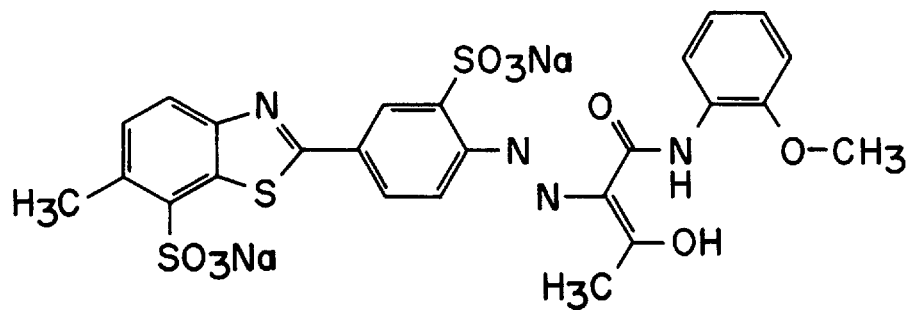
Figure 2C:
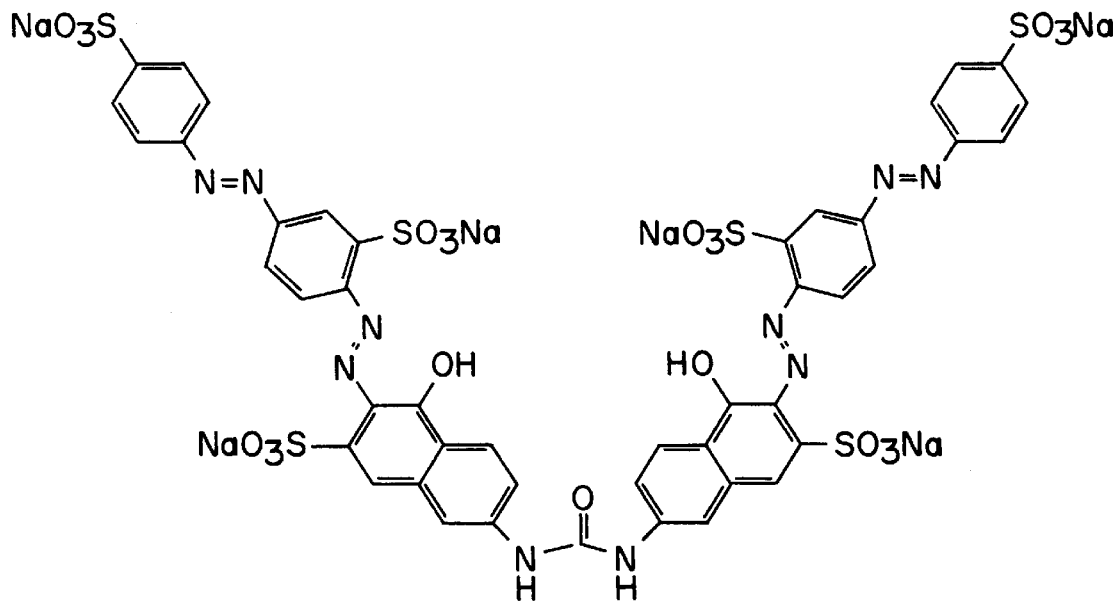

A sample containing TER3938, shown in FIG. 2B, also showed agonist activity. TER3938, shown in FIG. 2B and known as Direct Yellow No. 27, showed an $EC_{50}$ of 8 μM in this in vitro assay; it also enhanced the activity of insulin in stimulating autophosphorylation of insulin receptor on intact IM-9 cells. In addition, a sample containing TER3935, shown in FIG. 2C, was active in the IR kinase assay.

EXAMPLE 3

Identification of an Active Component of TER12 and TER3938-Containing Samples

Figure 3:
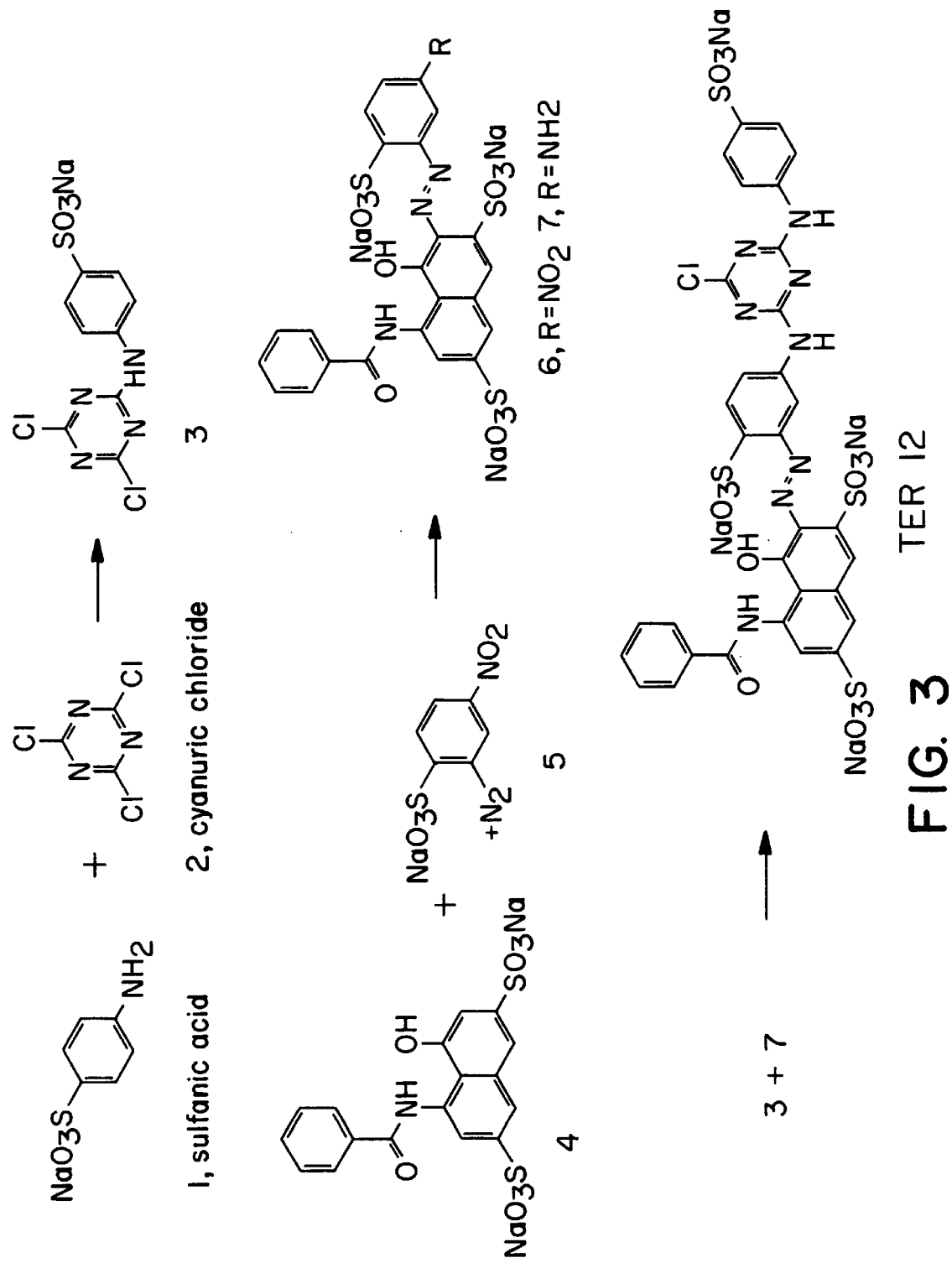
FIG. 3 shows the pathway for synthesis of TER12.

TER12 was synthesized by the reaction scheme shown in FIG. 3. TER12 synthesized using this scheme, and TER12 when extensively purified from commercial sources were active in the assays set forth in Example 1.

In addition, the sample containing TER3938, also obtained from commercial sources, when purified to 95% purity by reverse-phase HPLC, retained its activity; however, when this sample was washed with aqueous sodium carbonate, the insoluble compound shown in FIG. 2B as TER3938 was less active in the IR kinase assay; the aqueous layer, however, retained full activity. These results led to the conclusion that some of the activity shown in samples purportedly containing only TER12 and TER3938 was due to a minor component. This minor component was postulated to be Component A, which has the formula shown in FIG. 2F. Component A, obtained from commercial sources, was purified by C-18 reverse-phase preparative HPLC and retained its activity in the IR kinase assay. Component A was subsequently demonstrated to be a minor component in samples containing both TER12 and TER3938. No Component A was found in TER3935 which is active after extensive purification.

Figure 4:
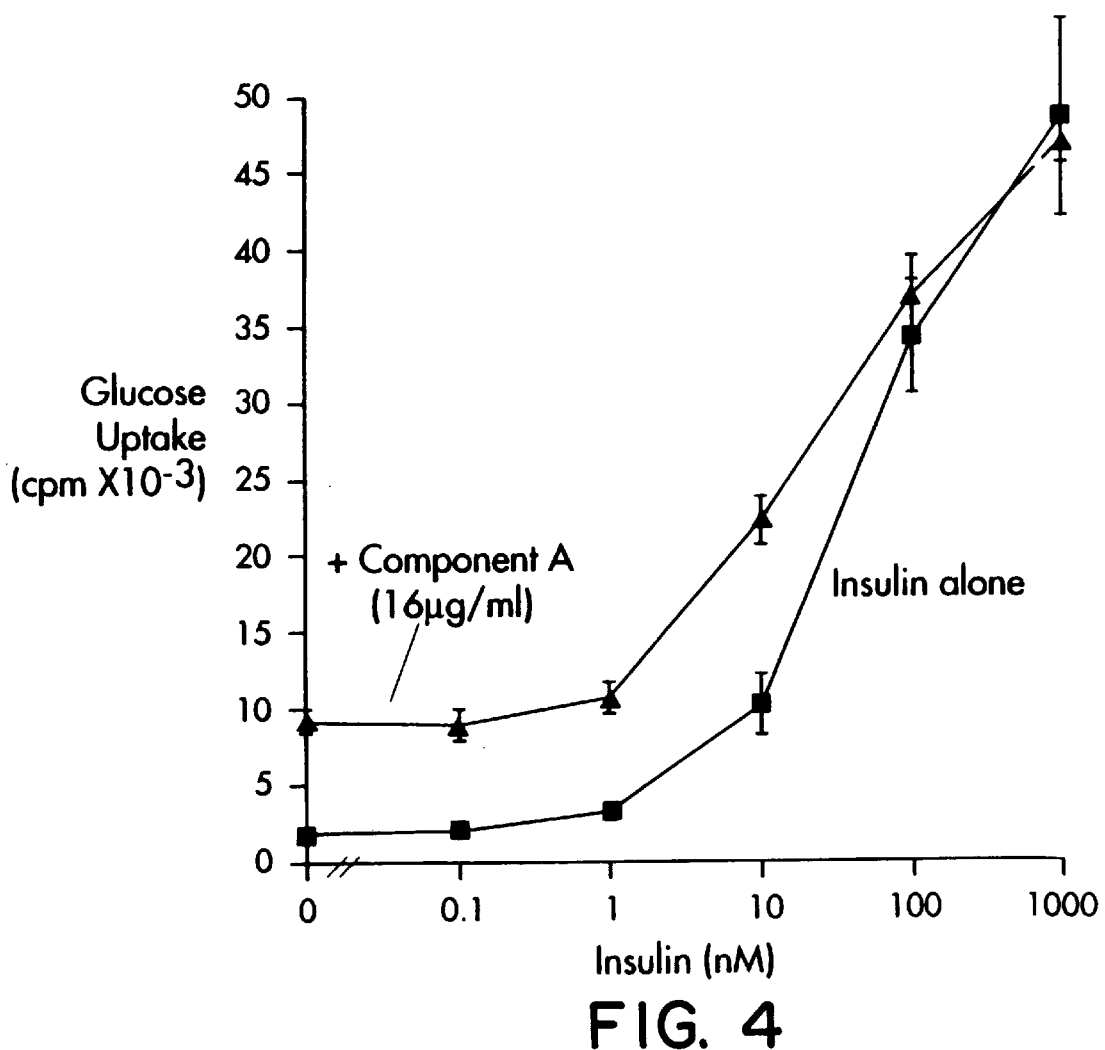
FIG. 4 shows the effect of Component A on insulin-induced uptake of glucose by adipocytes.

Component A, purified from a commercially supplied sample, enhances glucose uptake in differentiated 3T3-L1 cells, and the activity is not dependent on the presence of insulin. It is, however, dependent on the activity of PI-3 kinase, confirming that the glucose uptake is mediated via the insulin signaling pathway. The ability of 16 μg/ml concentrations of Component A to enhance glucose uptake at various insulin concentrations is shown in FIG. 4.

In the assay, 3T3-L1 pre-adipocytes were induced to differentiate into adipocyte morphology using standard protocols. Five days after induction, the cells were treated with 16 μg/ml of Component A in the presence of various levels of insulin for 30 minutes.

Glucose uptake was measured using $^{14}C$ glucose as label. As shown, 16 μg/ml of Component A alone effects uptake at approximately the level shown by 100 nM concentrations of insulin in the presence of this concentration of Component A.

EXAMPLE 4

Additional Compounds Related to TER3935

Figure 2D:
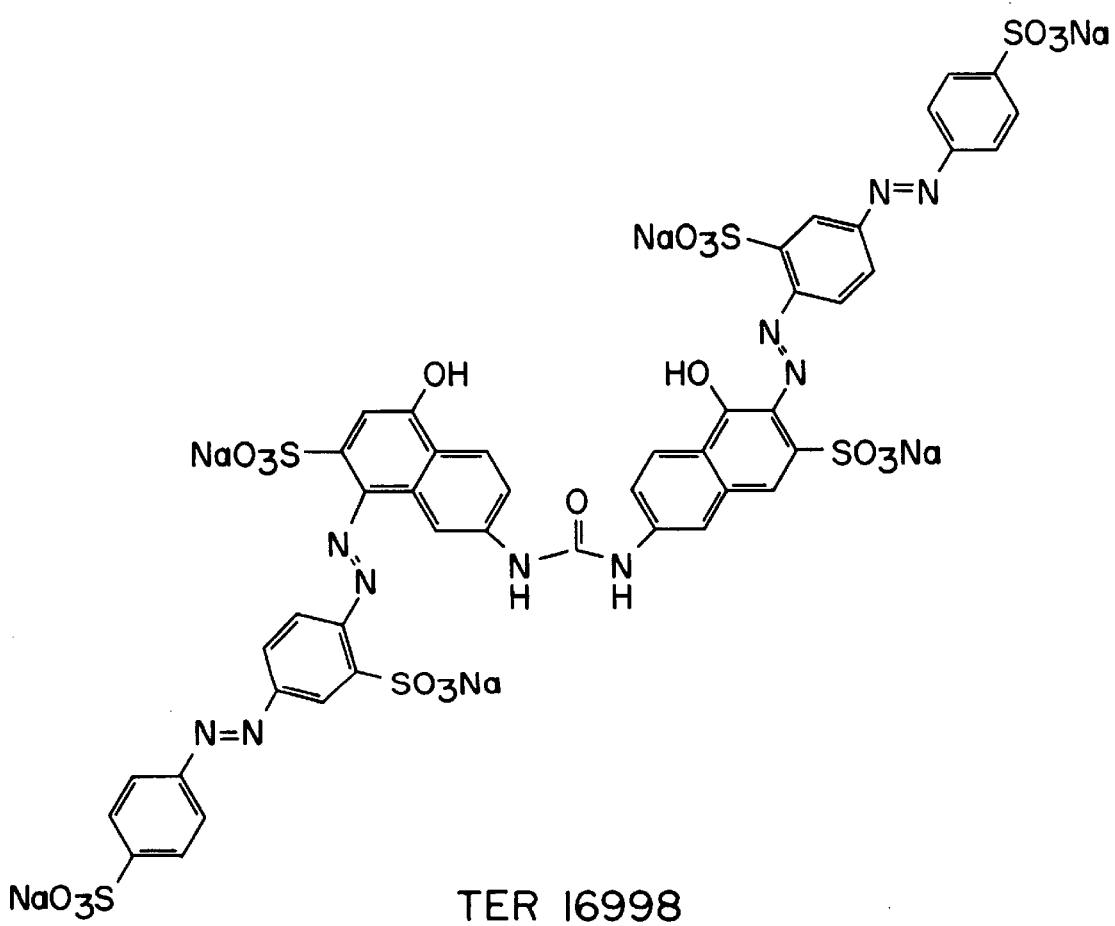
Figure 5:
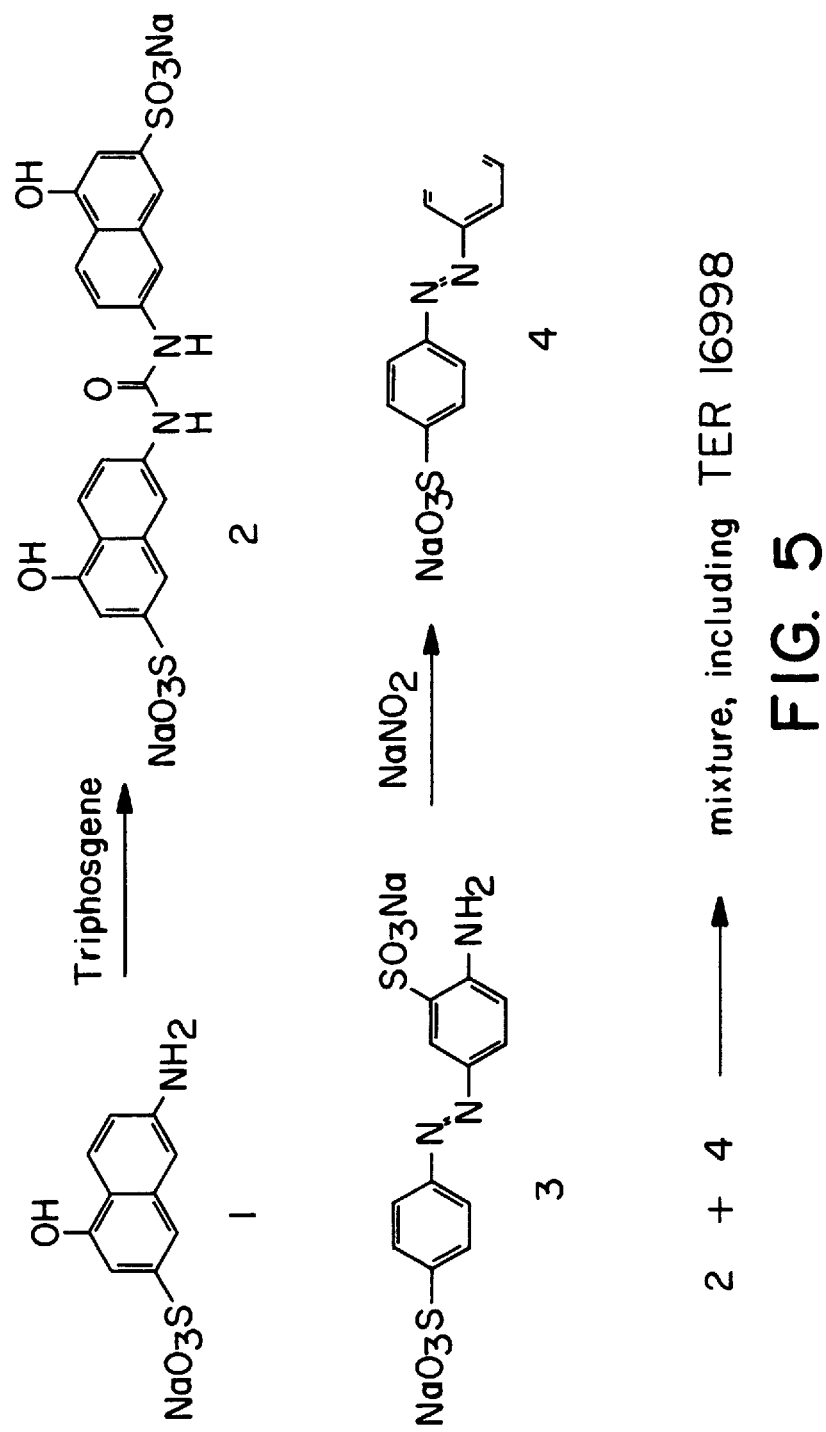
FIG. 5 shows the synthetic pathway for TER16998.

An additional compound with a structure regioisomeric to that of TER3935, TER116998, was isolated by preparative reverse-phase chromatography from the reaction mixture produced by the synthetic scheme shown in FIG. 5. Spectral data confirm that the isolated compound was of the formula shown in FIG. 2D.

Figure 6:
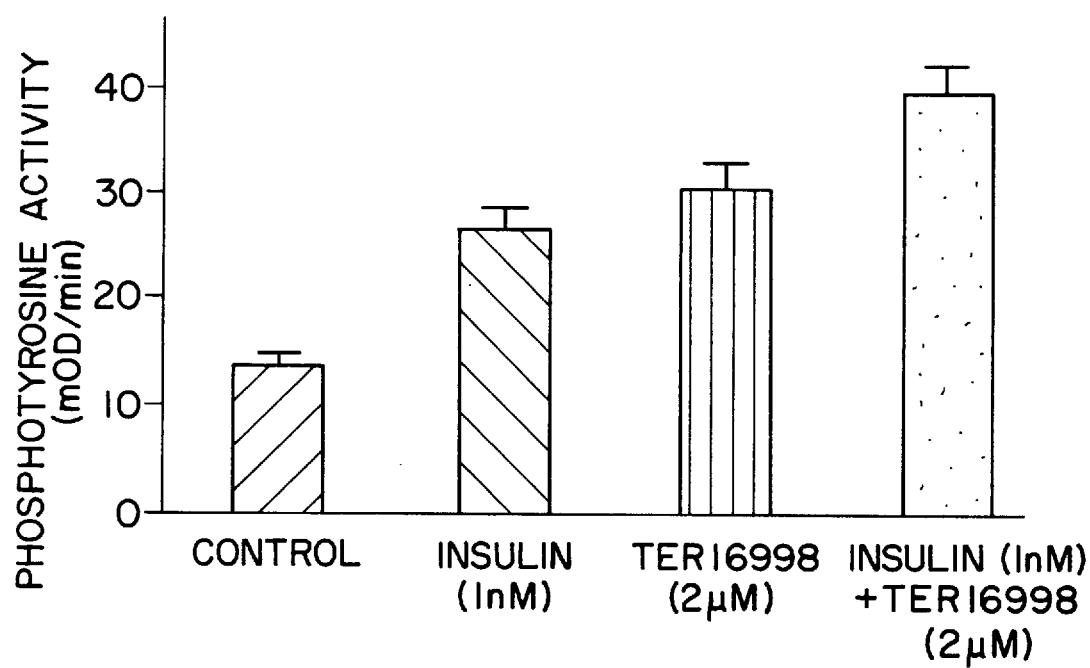
FIG. 6 shows the effect of TER16998, alone and in combination with insulin, on autophosphorylation of the IR receptor.

TER16998 activates the insulin receptor kinase directly, enhances autophosphorylation and substrate phosphorylation mediated through the insulin receptor, potentiates glucose transport and lowers blood glucose in the db/db mouse model of diabetes. These results were obtained as follows:

The assay described in Example 1, paragraph A, was conducted with a control lacking any additions, in the presence of insulin alone at 1 nM, in the presence of TER16998 at 2 μM, and in the presence of a combination of these components at the stated concentrations. As shown in FIG. 6, TER16998 alone is able to activate autophosphorylation of the receptor at this concentration, as well as to potentiate the effect of insulin.

Figure 7:
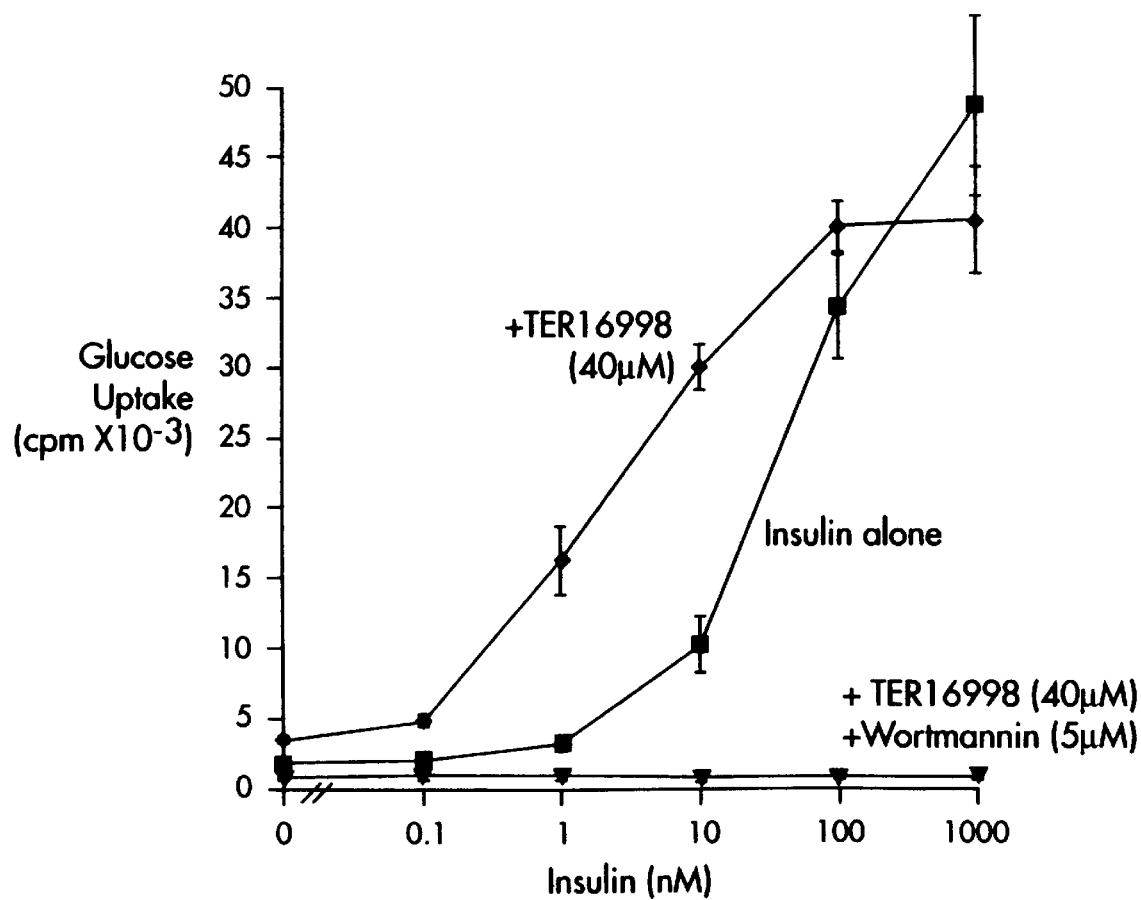
FIG. 7 shows the effect of TER16998 on insulin-induced glucose uptake in adipocytes.

In addition, in an assay for glucose uptake by 3T3-L1 adipocytes, described in Example 3, TER16998 produced an acute effect sensitizing the cells to insulin. This was inhibited, as expected, by 5 μM wortmannin which inhibits PI-3 kinase, confirming that TER16998 exerts its effect through the insulin-signaling pathway. These results are shown in FIG. 7. As shown, 40 μM of TER16998 potentiates the effect of insulin at a range of concentrations.

Significantly, TER16998 was not able to stimulate the phosphorylation activity of epidermal growth factor receptor in an EGF receptor kinase assay.

The effect of TER16998, of Component A, and of insulin on the distribution of the Glut4 transporter in 3T3-L1 adipocytes was determined by incubating the cells for 15 minutes with insulin or one of these compounds, after which the cells were fixed and stained with an anti-Glut4 antibody followed by FITC-conjugated secondary antibody. The results were visualized under a fluorescent microscope. The results showed that insulin and Component A produce a dramatic redistribution of Glut4 to the membrane surfaces whereas in untreated cells a diffuse pattern is obtained. TER16998 has a similar effect but less dramatic than that of insulin or Component A.

EXAMPLE 5

Effect of TER16998 in Diabetic Mice

Figure 8C:
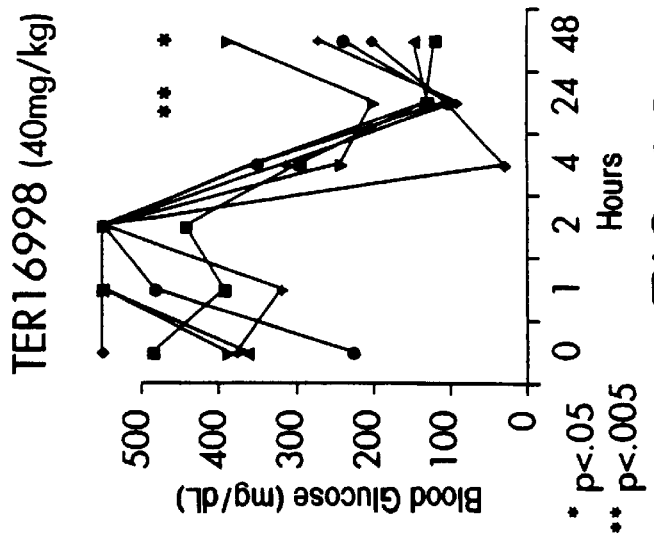
FIG. 8 shows the effect of TER16998 on blood glucose levels in a diabetic mouse model.
Figure 8B:
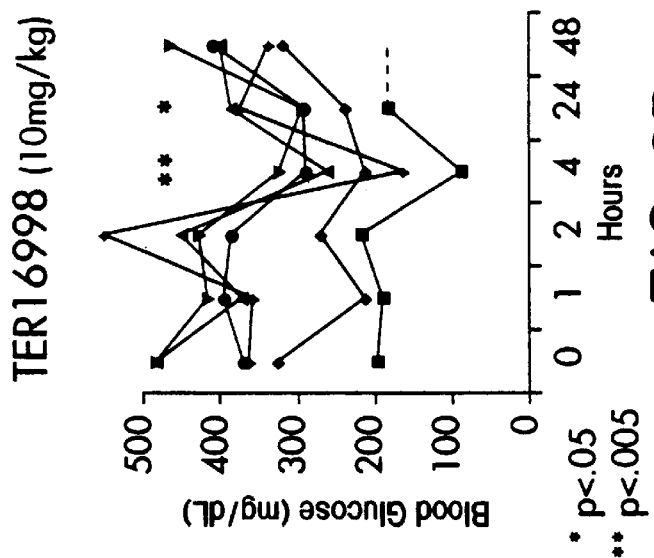
Figure 8A:
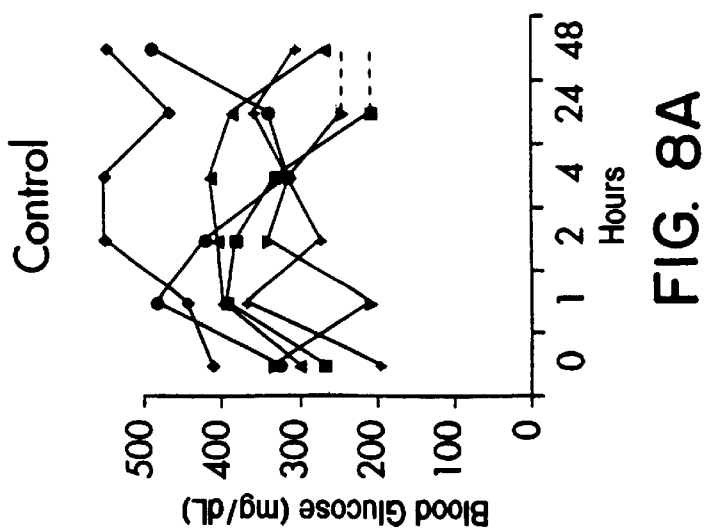

Mice which are standard models of Type II diabetes, db/db mice, were administered TER16998 at 10 mg/kg and 40 mg/kg, or a vehicle as a control. FIG. 8 shows the effect of this compound on the concentration of glucose in the blood of these animals. As shown in FIG. 8, 10 mg/kg to some extent and 40 mg/kg to an appreciable extent decrease blood glucose over a period of 24 hours from the time of administration.

EXAMPLE 6

Synthesis of Invention Compounds

Figure 9:
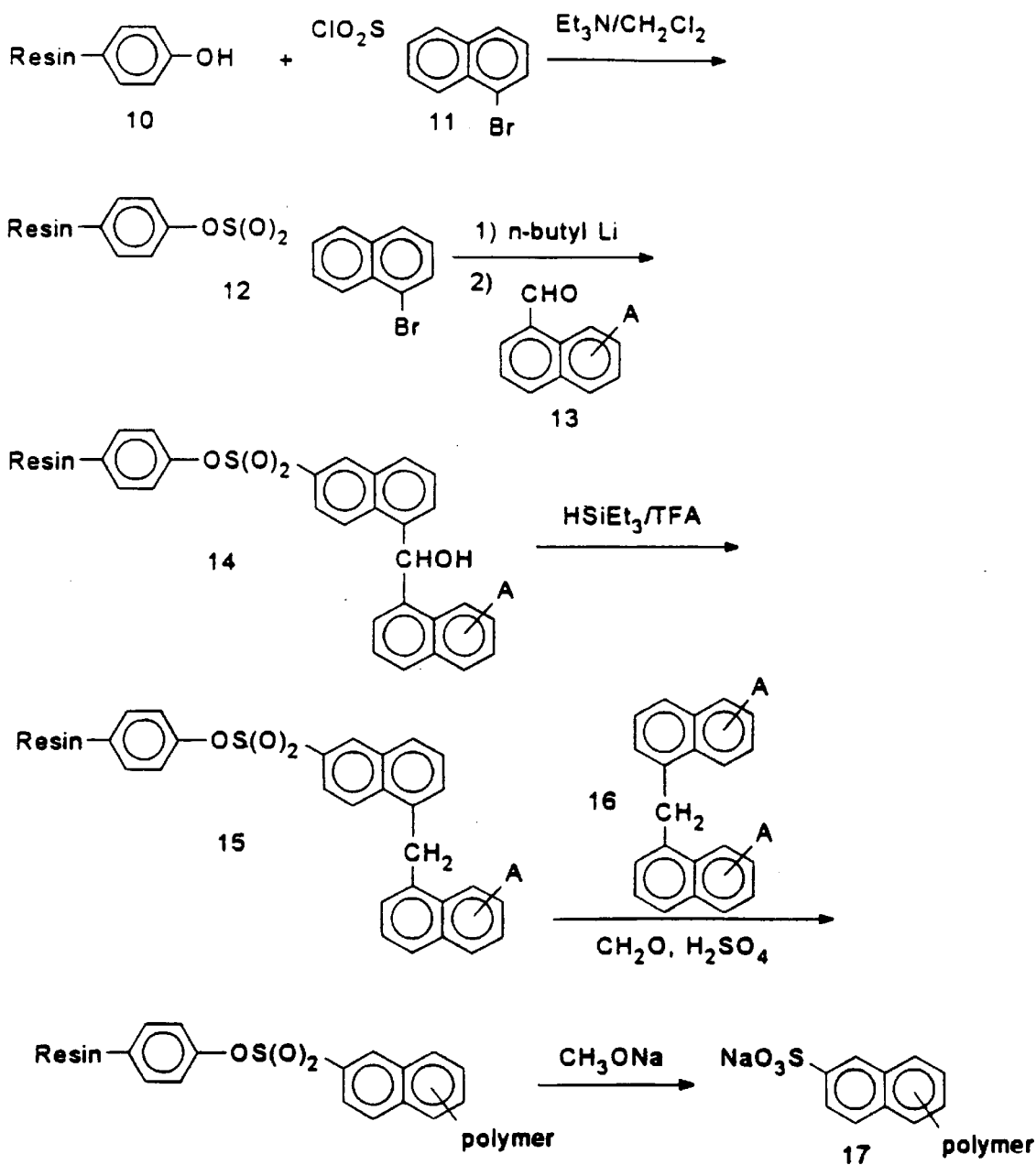
FIG. 9 shows the synthetic method for preparation of compounds similar to Component A.

The polymeric aromatic compounds of the invention are synthesized using either solution-phase or solid-phase-based syntheses. For solid-phase synthesis, the monomers are, for example, coupled to a phenolic resin of the formula 10 shown in FIG. 9. This phenolic resin is prepared by oxidation of the corresponding boronic ester polystyrene resin described by Farrall, M. J. and Frechet, J. M. J. *J Org Chem* (1976) 41:3877. The phenolic resin is condensed with an initial monomer, 11, as shown. The condensation product, 12, is treated with N-butyl lithium to replace the bromonium ion with lithium and this intermediate is condensed with a monomer, for example, of the formula 13, to provide the solid-supported dimer, 14. The linking —CHOH— can be, if desired, reduced to —CH$_2$—. Subsequent condensations in the presence of formaldehyde and concentrated sulfuric acid result in polymers of the desired length which can then be removed from the resin in sodium methoxide. This process is outlined in FIG. 9.

The synthesis can be varied by altering the nature of the monomer or dimer added to the supported starting group.

Synthesis of suitable oligomers is also conducted in solution phase. In one set of reactions, the synthesis is a variant of that described by Arduini, A. et al. *Tetrahedron* (1990) 46:3607–3613. Intermediate dimers or trimers are obtained by condensing an aromatic aldehyde with an aromatic bromide and further condensation is effected in the presence of formaldehyde and sulfuric acid. Dimers shown as formulas 18, 19 and 20, which contain the proton-accepting substituent in all possible configurations can be obtained by condensation of the appropriate naphthyl lithium with a naphthyl formyl derivative obtained by treating the naphthyl lithium with dimethyl formamide (DMF). If desired, compounds 18, 19 and 20 can be reduced with HSiEt$_3$/TFA to the corresponding methylene-bridged dinaphthylenes.

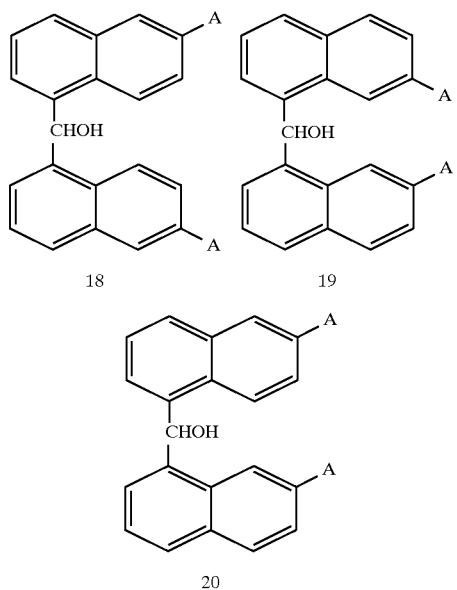

The dibromo dimer of the form 23 is obtained as described by Arduini, A. (supra) by condensing the corresponding naphthyl bromide with formaldehyde in the presence of sulfuric acid.

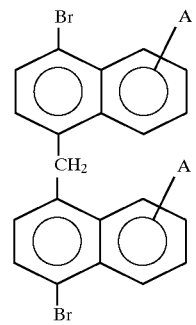

The corresponding trimers can be obtained by treating such bromo-substituted dimers with N-butyl lithium and then with an aldehyde of the formula 21 or 22.

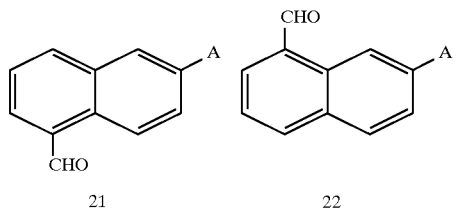

The oligomers may also be extended by coupling naphthyl or other aromatic moieties with dialdehydes, for example, 4,4'-biphenyldicarboxaldehyde or terephthaldehyde.

By appropriate choice of the position of the proton-accepting substituent A, and of the reactive substituents on the aromatic moieties, the desired oligomers may be synthesized.

As set forth above, the polymer of the formula

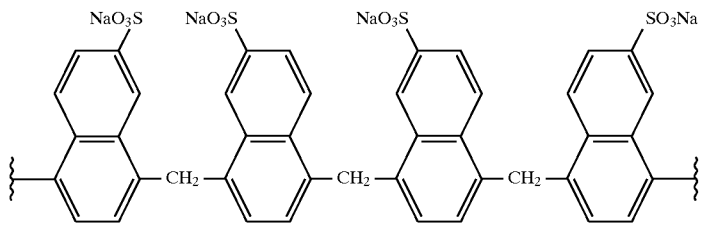

Component A is active in the insulin receptor kinase assay described above and exhibits the ability to potentiate insulin activation and glucose uptake.

We claim:

1. A method to modulate the kinase activity of insulin receptor which method comprises contacting said insulin receptor or the kinase portion thereof with a compound of the formula

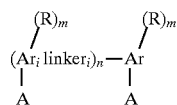

Formula (1)

wherein each Ar is independently an aromatic moiety, each A is independently a proton-accepting substituent; each R is independently a noninterfering substituent; m is 0 or 1; n is 4–6; and each linker is independently an isostere of —CH$_2$—, —CH=CH— or —NHCO—.

2. The method of claim 1 wherein each A is independently —SO$_3$X or —COOX wherein X is H or a cation.

3. The method of claim 1 wherein each R is independently alkyl (1–6C).

4. The method of claim 1 wherein all m are 0.

5. The method of claim 1 wherein said compound is of the formula

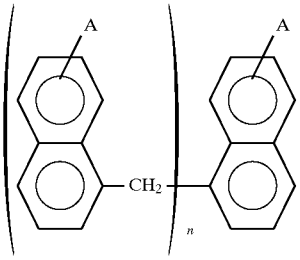

wherein n is 4–6 and A is as defined in claim 1.

6. A method to potentiate the insulin activation of insulin receptor which method comprises contacting said insulin receptor or the kinase portion thereof with insulin and with a compound of the formula

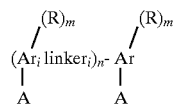

Formula (1)

wherein each Ar is independently an aromatic moiety; each A is independently a proton-accepting substituent; each R is independently a noninterfering substituent; m is 0 or 1; n is 4–6; and each linker is independently an isostere of —CH$_2$—, —CH=CH— or —NCHO—;

said compound provided in an amount effective to potentiate said insulin activation.

7. The method of claim 6 wherein each A is independently —SO$_3$X or —COOX wherein X is H or a cation.

8. The method of claim 6 wherein each R is independently alkyl(1–6C).

9. The method of claim 6 wherein all m are 0.

10. The method of claim 6 wherein said compound is of the formula

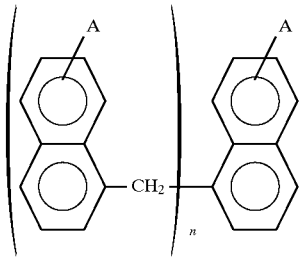

wherein n is 4–6 and A is as defined in claim 1.

* * * * *